(12) United States Patent
Edie et al.

(10) Patent No.: US 7,935,148 B2
(45) Date of Patent: May 3, 2011

(54) ADJUSTABLE INSERTION DEVICE FOR A VERTEBRAL IMPLANT

(75) Inventors: Jason A. Edie, Memphis, TN (US); James Douglas Schwender, Edina, MN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 760 days.

(21) Appl. No.: 11/327,889

(22) Filed: Jan. 9, 2006

(65) Prior Publication Data

US 2007/0162129 A1    Jul. 12, 2007

(51) Int. Cl.
*A61F 2/44* (2006.01)
(52) U.S. Cl. ............... 623/17.16; 623/17.11; 606/99
(58) Field of Classification Search ............... 623/17.16, 623/17.11, 17.12, 17.13, 17.14, 17.15; 606/246, 606/99, 100, 914, 915–916; 81/121.1
See application file for complete search history.

(56) References Cited

U.S. PATENT DOCUMENTS

| | | |
|---|---|---|
| 2,876,777 A | 3/1959 | Kees, Jr. |
| 3,848,601 A | 11/1974 | Ma et al. |
| 3,916,907 A | 11/1975 | Peterson |
| 4,306,550 A | 12/1981 | Forte |
| 4,401,112 A | 8/1983 | Rezaian |
| 4,545,374 A | 10/1985 | Jacobson |
| 4,573,448 A | 3/1986 | Kambin |
| 4,646,738 A | 3/1987 | Trott |
| 4,657,550 A | 4/1987 | Daher |
| 4,714,469 A | 12/1987 | Kenna |
| 4,736,738 A | 4/1988 | Lipovsek et al. |
| 4,743,256 A | 5/1988 | Brantigan |
| 4,820,305 A | 4/1989 | Harms et al. |
| 4,834,757 A | 5/1989 | Brantigan |
| 4,932,975 A | 6/1990 | Main et al. |
| 5,026,373 A | 6/1991 | Ray et al. |
| 5,062,850 A | 11/1991 | MacMillan et al. |
| 5,123,310 A * | 6/1992 | McManus ............... 81/125 |
| 5,217,463 A | 6/1993 | Mikhail |
| 5,250,061 A | 10/1993 | Michelson |
| 5,336,223 A | 8/1994 | Rogers |
| 5,344,459 A | 9/1994 | Swartz |
| 5,395,317 A | 3/1995 | Kambin |
| 5,397,364 A | 3/1995 | Kozak et al. |
| 5,403,317 A | 4/1995 | Bonutti |
| 5,431,658 A | 7/1995 | Moskovich |
| 5,439,464 A | 8/1995 | Shapiro |
| 5,484,437 A | 1/1996 | Michelson |
| 5,514,180 A | 5/1996 | Heggeness et al. |
| 5,571,190 A | 11/1996 | Ulrich et al. |
| 5,571,192 A | 11/1996 | Schonhoffer |

(Continued)

FOREIGN PATENT DOCUMENTS

DE          27 32 325 A1    1/1979

(Continued)

*Primary Examiner* — Eduardo C Robert
*Assistant Examiner* — Jan Christopher Merene (57) ABSTRACT

Methods and devices for connecting an insertion device to an implant. The insertion device includes a body having first and second ends. The first end may be configured to connect with the implant. The first end may be selectively positionable between orientations to provide for the connection. Methods of positioning the implant within the patient generally include connecting the insertion device to the implant. The insertion device can then be manipulating to position the implant within the patient. The insertion device is removed from the implant once positioned, or may be reconnected at another location to further position the implant.

17 Claims, 6 Drawing Sheets

U.S. PATENT DOCUMENTS

| | | | |
|---|---|---|---|
| 5,586,989 | A | 12/1996 | Bray, Jr. |
| 5,599,279 | A | 2/1997 | Slotman et al. |
| 5,607,424 | A | 3/1997 | Tropiano |
| 5,609,635 | A | 3/1997 | Michelson |
| 5,609,636 | A | 3/1997 | Kohrs et al. |
| 5,609,637 | A | 3/1997 | Biedermann et al. |
| 5,620,458 | A | 4/1997 | Green et al. |
| 5,688,284 | A | 11/1997 | Chervitz et al. |
| 5,697,889 | A | 12/1997 | Slotman et al. |
| 5,702,451 | A | 12/1997 | Biedermann et al. |
| 5,702,453 | A | 12/1997 | Rabbe et al. |
| 5,702,455 | A | 12/1997 | Saggar |
| 5,720,748 | A | 2/1998 | Kuslich et al. |
| 5,730,754 | A | 3/1998 | Obenchain |
| 5,741,253 | A | 4/1998 | Michelson |
| 5,741,261 | A | 4/1998 | Moskovitz et al. |
| 5,755,732 | A | 5/1998 | Green et al. |
| 5,766,252 | A | 6/1998 | Henry et al. |
| 5,772,661 | A | 6/1998 | Michelson |
| 5,776,199 | A | 7/1998 | Michelson |
| 5,836,948 | A | 11/1998 | Zucherman et al. |
| 5,857,995 | A | 1/1999 | Thomas et al. |
| 5,860,973 | A | 1/1999 | Michelson |
| 5,860,977 | A | 1/1999 | Zucherman et al. |
| 5,861,041 | A | 1/1999 | Tienboon |
| 5,888,224 | A | 3/1999 | Beckers et al. |
| 5,893,890 | A | 4/1999 | Pisharodi |
| 5,925,056 | A | 7/1999 | Thomas et al. |
| 5,951,564 | A | 9/1999 | Schroder et al. |
| 5,961,522 | A | 10/1999 | Mehdizadeh |
| 5,968,062 | A | 10/1999 | Thomas et al. |
| 5,972,031 | A | 10/1999 | Biedermann et al. |
| 5,980,522 | A * | 11/1999 | Koros et al. ............... 623/17.11 |
| 5,984,922 | A | 11/1999 | McKay |
| 5,989,290 | A | 11/1999 | Biedermann et al. |
| 6,015,436 | A | 1/2000 | Schonhoffer |
| 6,059,829 | A * | 5/2000 | Schlapfer et al. .......... 623/17.16 |
| 6,074,390 | A | 6/2000 | Zucherman et al. |
| 6,086,613 | A | 7/2000 | Camino et al. |
| 6,102,930 | A | 8/2000 | Simmons, Jr. |
| 6,102,949 | A | 8/2000 | Biedermann et al. |
| 6,110,175 | A | 8/2000 | Scholl |
| 6,113,639 | A | 9/2000 | Ray et al. |
| 6,126,664 | A | 10/2000 | Troxell et al. |
| 6,143,032 | A | 11/2000 | Schafer et al. |
| 6,149,651 | A | 11/2000 | Drewry et al. |
| 6,159,215 | A | 12/2000 | Urbahns et al. |
| 6,174,311 | B1 | 1/2001 | Branch |
| 6,176,882 | B1 | 1/2001 | Biedermann et al. |
| 6,190,413 | B1 | 2/2001 | Sutcliffe |
| 6,193,755 | B1 | 2/2001 | Metz-Stavenhagen et al. |
| 6,224,603 | B1 | 5/2001 | Marino |
| 6,241,771 | B1 | 6/2001 | Gresser et al. |
| 6,245,108 | B1 | 6/2001 | Biscup |
| 6,258,125 | B1 | 7/2001 | Paul et al. |
| 6,261,296 | B1 | 7/2001 | Aebi et al. |
| 6,290,724 | B1 | 9/2001 | Marino |
| 6,319,257 | B1 | 11/2001 | Carignan et al. |
| 6,432,106 | B1 | 8/2002 | Fraser |
| 6,436,101 | B1 | 8/2002 | Hamada |
| 6,719,794 | B2 | 4/2004 | Gerber et al. |
| 6,824,565 | B2 | 11/2004 | Muhanna et al. |
| 6,855,168 | B2 * | 2/2005 | Crozet ....................... 623/17.11 |
| 6,881,228 | B2 | 4/2005 | Zdeblick et al. |
| 6,974,480 | B2 * | 12/2005 | Messerli et al. ........... 623/17.16 |
| 7,503,933 | B2 * | 3/2009 | Michelson .................. 623/17.11 |
| 2002/0045904 | A1 | 4/2002 | Fuss et al. |
| 2002/0055781 | A1 | 5/2002 | Sazy |
| 2002/0077700 | A1 | 6/2002 | Varga et al. |
| 2002/0120334 | A1 * | 8/2002 | Crozet ....................... 623/17.11 |
| 2002/0165612 | A1 | 11/2002 | Gerber et al. |
| 2003/0078668 | A1 * | 4/2003 | Michelson .................. 623/17.16 |
| 2003/0100950 | A1 | 5/2003 | Moret |
| 2003/0139813 | A1 * | 7/2003 | Messerli et al. ........... 623/17.11 |
| 2003/0181981 | A1 | 9/2003 | Lemaire |
| 2004/0138751 | A1 * | 7/2004 | Michelson .................. 623/17.11 |
| 2005/0038431 | A1 * | 2/2005 | Bartish et al. .................... 606/61 |
| 2005/0096745 | A1 * | 5/2005 | Andre et al. ................ 623/17.11 |
| 2008/0091211 | A1 * | 4/2008 | Gately ............................ 606/99 |
| 2009/0276049 | A1 * | 11/2009 | Weiland ..................... 623/17.16 |

FOREIGN PATENT DOCUMENTS

| | | |
|---|---|---|
| DE | 195 09 317 A1 | 9/1996 |
| DE | 29901611 U1 | 4/1999 |
| DE | 199 03 763 A1 | 8/2000 |
| EP | 0 33 990 A2 | 9/1989 |
| EP | 0613 662 A2 | 11/1993 |
| EP | 0 916 323 A1 | 5/1999 |
| FR | 2 636 227 | 3/1990 |
| FR | 2 736 537 | 1/1997 |
| FR | 2 742 653 | 6/1997 |
| FR | 2 767 675 | 3/1999 |
| FR | 2 808 673 | 11/2001 |
| WO | WO 97/14378 | 4/1997 |
| WO | WO 97/32547 | 9/1997 |
| WO | WO 98/20939 | 5/1998 |
| WO | WO 98/56319 | 12/1998 |
| WO | WO/9937255 | 7/1999 |
| WO | WO 00/44288 | 8/2000 |
| WO | WO 01/28469 A2 | 4/2001 |
| WO | WO 01/70144 A1 | 9/2001 |
| WO | WO 01/95838 A1 | 12/2001 |
| WO | WO 02/17823 | 3/2002 |

\* cited by examiner

ADJUSTABLE INSERTION DEVICE FOR A VERTEBRAL IMPLANT

The present application is directed to an insertion device and methods for inserting and/or placing an implant in a patient. More specifically, the application is directed to devices and methods of connecting the insertion device to the implant.

BACKGROUND

An insertion device is often necessary for inserting an implant into a patient. The implant may have a variety of sizes and shapes to fit within the space between vertebral members, or other spaces within the patient. The implant may become a permanent fixture within the patient, or a temporary fixture inserted for a limited period of time. One specific example includes a trial implant initially inserted into the patient and later replaced by another trial or permanent fixture.

Current methods for insertion and/or positioning of the implant within the patient require a surgeon to use several freehand instruments. This requires that the surgeon manipulate several different instruments at a time to insert and move the implant. Using multiple instruments may be physically difficult for the surgeon, as well as mentally taxing and frustrating.

Another drawback of some current methods is inability to connect the insertion device to the implant. This makes positioning of the implant difficult because the insertion device may slide or skid off of the implant causing neural and tissue damage. If the insertion device is able to connect to the implant in current methods, the connection may not provide for adjustment to facilitate insertion and positioning. Further, it may be difficult to disconnect the insertion device from the implant after positioning is complete. Detaching the insertion device may cause the implant to move within the patient, thus eliminating the advantages of being able to accurately locate the implant initially.

SUMMARY

The present application is directed to methods and devices for connecting an insertion device to an implant. The insertion device includes a body having first and second ends. The first end is configured to connect with the implant. The first end may be selectively positionable between orientations to provide for the connection.

Methods of positioning the implant within the patient generally include connecting the insertion device to the implant. The insertion device can then be manipulating to position the implant within the patient. The insertion device is removed from the implant once positioned, or may be reconnected at another location to further position the implant.

DETAILED DESCRIPTION

Figure 1:
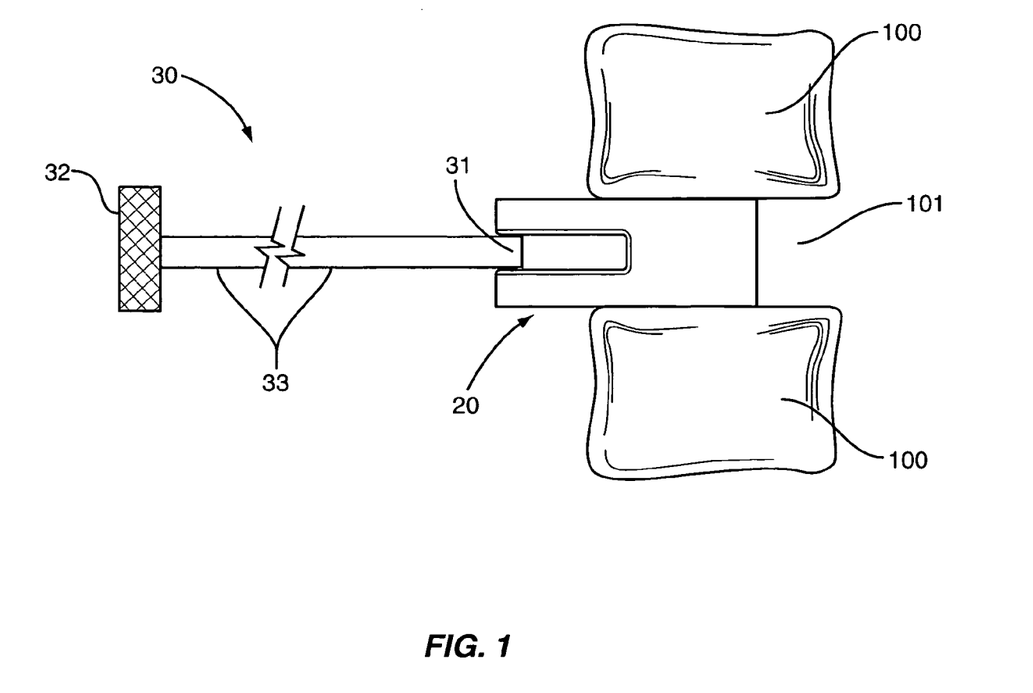
FIG. 1 is a schematic diagram of an insertion device connected to an implant according to one embodiment.

The present application is directed to devices and methods for positioning an implant within a patient. FIG. 1 schematically illustrates one embodiment of an insertion device 30 connected to an implant 20. The insertion device 30 comprises a body 33 having a first end 31 that connects to the implant 20, and a second end 32 that is manipulated by the surgeon. In this embodiment, the implant 20 is positioned within a space 101 between vertebral members 100. Insertion device 30 connects to the implant 20 for positioning the implant within the patient. Once positioned, insertion device 30 may be removed while maintaining the position of the implant 20.

Figure 2:
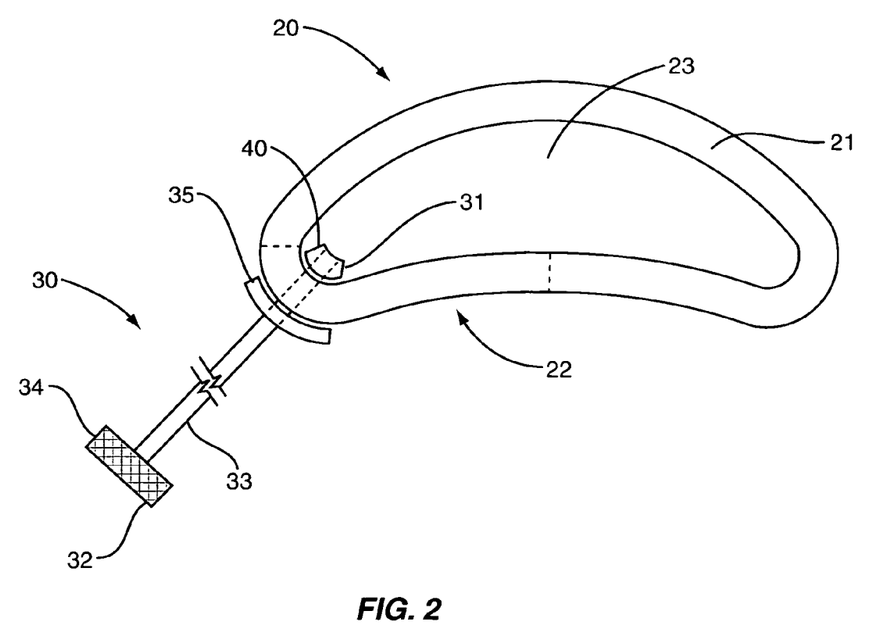
FIG. 2 is a top view of an insertion device connected to an implant according to one embodiment.
Figure 3:
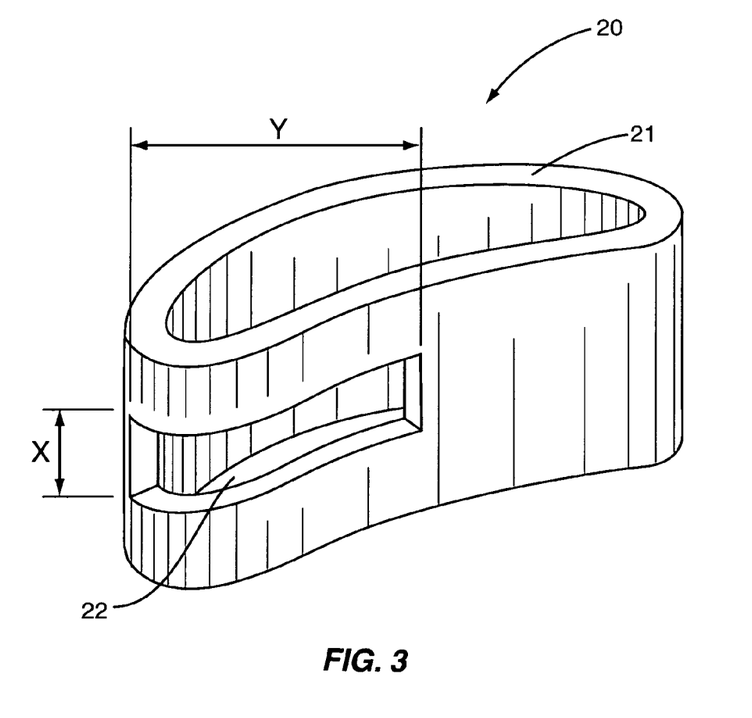
FIG. 3 is a perspective view of an implant according to one embodiment.

FIGS. 2 and 3 illustrate one embodiment of the insertion device 30 and implant 20. Implant 20 includes an interior section 23 defined by a wall 21. Implant 20 may have a variety of shapes and sizes. In this embodiment, the shape and size is configured to fit within a section of the disc space 101 defined between vertebral members 100. An opening 22 is positioned within the wall 21 and extends into the interior section 23.

A connection member 40 is positioned to receive the distal end 31 of the insertion device 30. In one embodiment, the connection member 40 is positioned within the interior section 23. The connection member 40 is larger than the opening 22 thus preventing escape. In another embodiment, connection member 40 is positioned within the wall 21 to extend across a section of the opening 22. Member 40 in this embodiment has a size and shape to move along the length of the opening 22, yet is contained within the wall such that it cannot be removed through the opening 22.

The insertion device 30 includes a body 33 having a distal end 31 and proximal end 32. The distal end 31 connects to the connection member 40. The method of connection between the insertion device 30 and the implant 20 may vary depending upon the context. Examples of connections include threaded engagement, press fit, taper fit, and key lock. The second end 32 is equipped with an actuator 34 that is operatively connected to the distal end 31. Movement of the actuator 34, such as rotation or pulling or pushing, results in the distal end 31 becoming engaged or disengaged from the connection member 40. In one embodiment, the body 33 has an elongated length to position the actuator 34 outside of the patient while the distal end 31 is connected to the connection member 40. In one embodiment, insertion device 30 includes a first elongated member including the actuator 34 and distal end 31, and an outer sleeve that extends between the actuator 34 and distal end 31. A stop 35 may be attached to the body 33 between the distal and proximal ends 31, 32. Stop 35 is fixedly attached to the body 33 and controls the depth of insertion of the distal end 31 relative to the implant 20.

One method of use includes connecting the insertion device 30 to the implant 20 prior to insertion into the patient.

Connecting comprises positioning the distal end 31 within the connection member 40 and using the actuator 34 to connect the elements together. In one embodiment, actuator 34 tightens the distal end 31 to the connection member 40 until the stop 35 is placed in contact with an outer surface of the wall 21. The wall 21 is compressed between the connection member 40 and stop 35 to further maintain connection to the implant 20. Once connected, the surgeon can manipulate the proximal end 32 to insert and position the implant 20. During use, the actuator 34 can loosen the distal end 31 and connection member 40 to reposition the insertion device 30 relative to the implant 20. Once repositioned, actuator 34 tightens the member 40 to the distal end 31 and the surgeon can again position the implant 20. Once the implant 20 is positioned, the distal end 31 is removed from the connection member 40 and the insertion device 30 is removed from the patient.

In one embodiment, connection member 40 remains within the implant 20 after removal of the insertion device 30. In one embodiment, connection member 40 dissipates within the implant 20 due to its construction which may be dissolvable, resorbable, or water soluble. In another embodiment, connection member 40 remains within the interior section 23 (i.e., does not dissipate).

Figure 4:
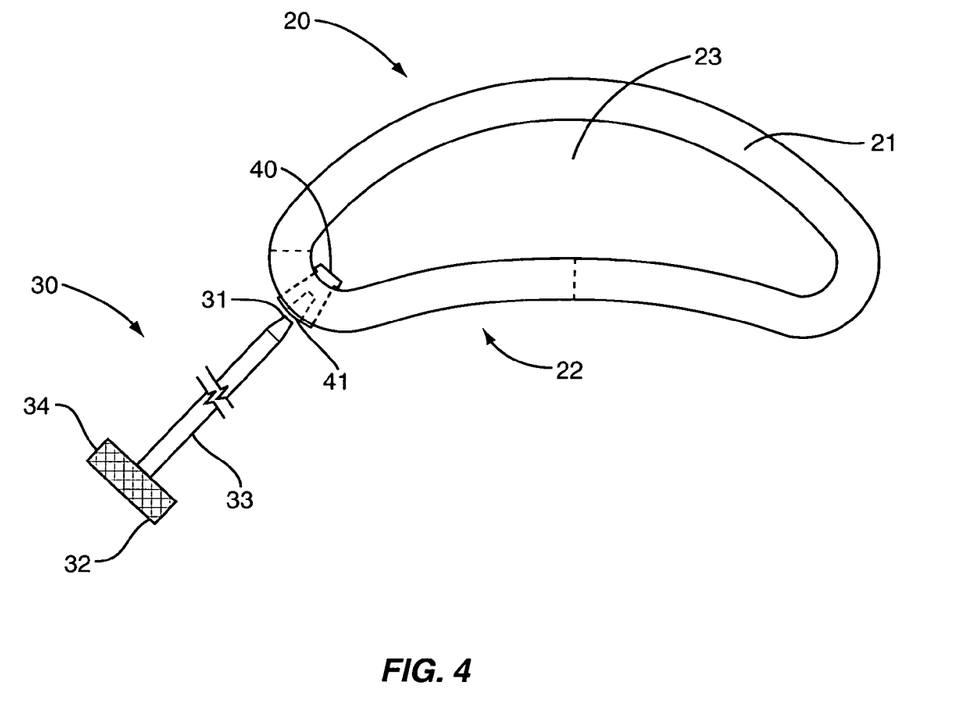
FIG. 4 is a top view of an insertion device and a connection member within an implant according to one embodiment.

FIG. 4 illustrates another embodiment with the connection member 40 captured within the implant wall 21. Connection member 40 includes a receiving area 41 for receiving the distal end 31 of the insertion device 30. The connection member 40 may be fixedly positioned within the implant opening 22, or movable along the length of the opening 22. In one embodiment, the connection member 40 is movable within the opening 22 when the insertion device 30 is removed. Insertion of the distal end 31 causes the distal end 31 to expand thus preventing additional movement along the opening 22. Connection of the distal end 31 to the connection member 40 may be by a variety of methods, such as a threaded connection, press fit, taper fit, and key lock.

Positioning the connection member 40 within the opening 22 may be accomplished by a variety of methods. One method includes shrinking the connection member 40 using liquid nitrogen. Once the connection member 40 is correctly oriented and warmed to room temperature, the member 40 is captured and free to move or not move as appropriate.

In one embodiment, two or more openings 22 may be positioned along the implant 22 each sized to connect with the insertion device 30 for placement of the implant 20. In one embodiment, insertion device 30 is connected to a first opening for initial positioning within the patient, and then re-connected to a second opening for additional positioning. The multiple openings may have the same or different sizes and shapes. Additionally, the multiple openings may feature a different connection method.

Figure 5:
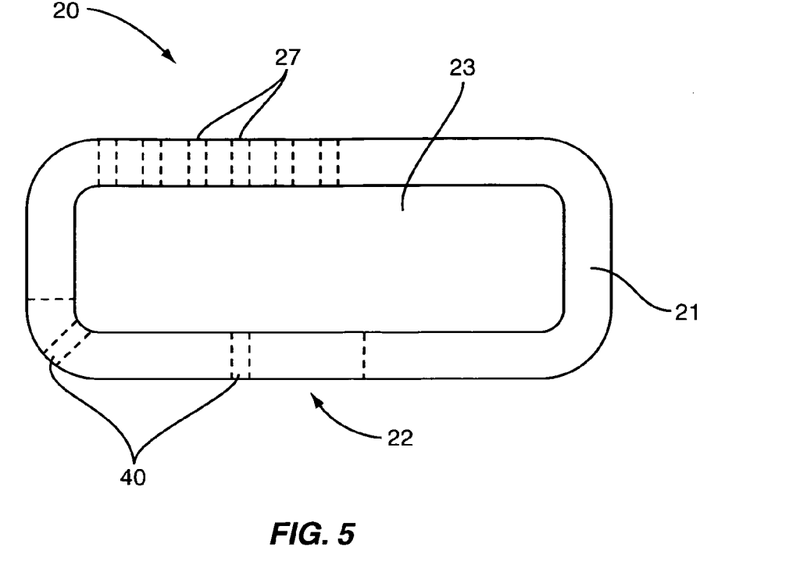
FIG. 5 is a top view of an implant according to one embodiment.

FIG. 5 illustrates an embodiment having multiple openings for connection with the insertion device 30. Opening 22 extends along a section of the wall 21 and includes two or more connection members 40. Openings 27 are positioned opposite from opening 22. Each opening 27 is sized to receive the distal end 30, and may provide for a number of different connection means. Openings 27 may be used in combination with opening 22, or independently.

One method of using this implant 20 is inserting the distal end 31 through the connection member 40 within opening 22 and into an opening 27. This double connection secures the implant 20 to the insertion device 30 and prevents inadvertent disconnection. In another method of use, insertion device 30 is initially connected within opening 22 or opening 27 and positioned within the patient. Insertion device 30 may then be disconnected and connected to the other of opening 22 or 27 to further position the implant 20 within the patient.

Figure 6:
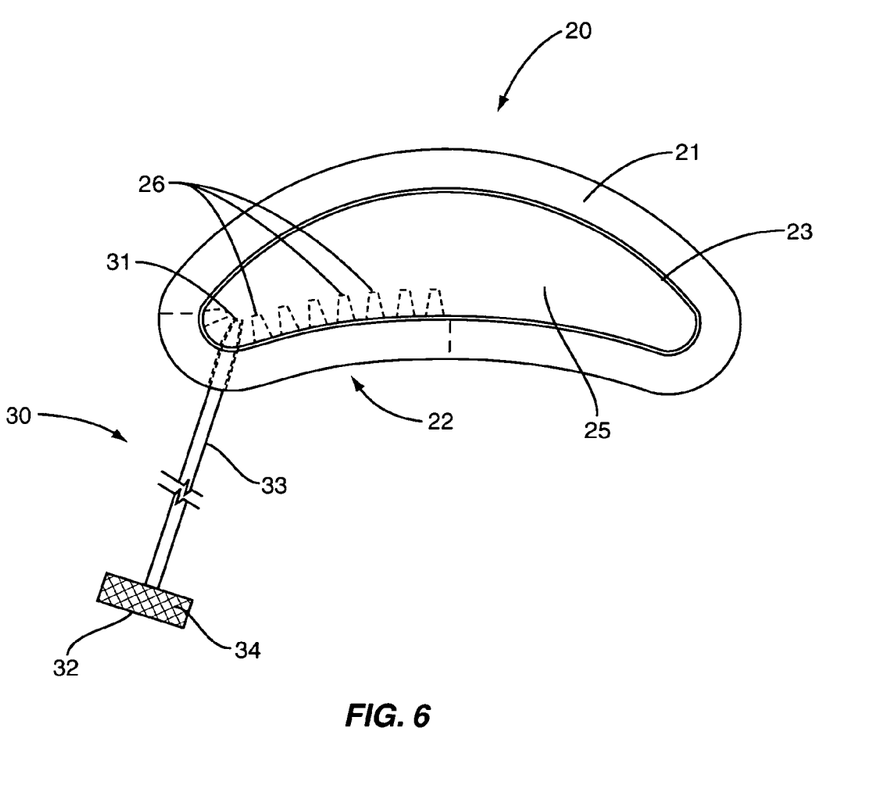
FIG. 6 is a top view of an insertion device and a connection member within an implant according to one embodiment.

FIG. 6 illustrates another embodiment for connecting the insertion device 30 to the implant 20. Implant 20 includes an outer wall 21 defining an interior section 23. An inner member 25 is positioned within the interior section 23 and includes one or more connection members 26 for receiving the distal end 31 of the insertion device 30. The inner member 25 may comprised of a single or multiple sections. The inner member 25 may be movable within the interior section 25, or fixedly positioned. Inner member 25 may be constructed of a material such as PEEK or titanium, or may also be constructed of a material that dissipates within the implant 20.

Connection members 26 are aligned with the opening 22. In the embodiment illustrated in FIG. 6, a number of connection members 26 are positioned within the inner member 25 and each sized and configured to receive and connect with the distal end 31. The different connection members 26 are positioned along the length of the opening 22 to facilitate connection with the distal end 31 and positioning within the patient. Connection members 26 are configured to connect with the distal end 31 and may be threaded to mate with a threaded distal end. Other connection configurations may include press fit, taper fit, and key lock. Each of the connection members 26 may be the same shape and configuration, or there may be a variety of different shapes and configurations. By way of example, a first connection 26 may be threaded and a second connection 26 may provide for a press fit.

Use of the embodiment of FIG. 6 may include connecting the distal end 31 within one of the connection members 26. The surgeon may then manipulate the insertion device 30, and particularly the second end 32, to position the implant 20 within the patient. Once the implant 20 is positioned, the insertion device 30 is removed from the implant 20 which remains within the patient. Alternatively, the insertion device 30 may be re-connected to another connection member 26 to further position the implant 20.

Figure 7:
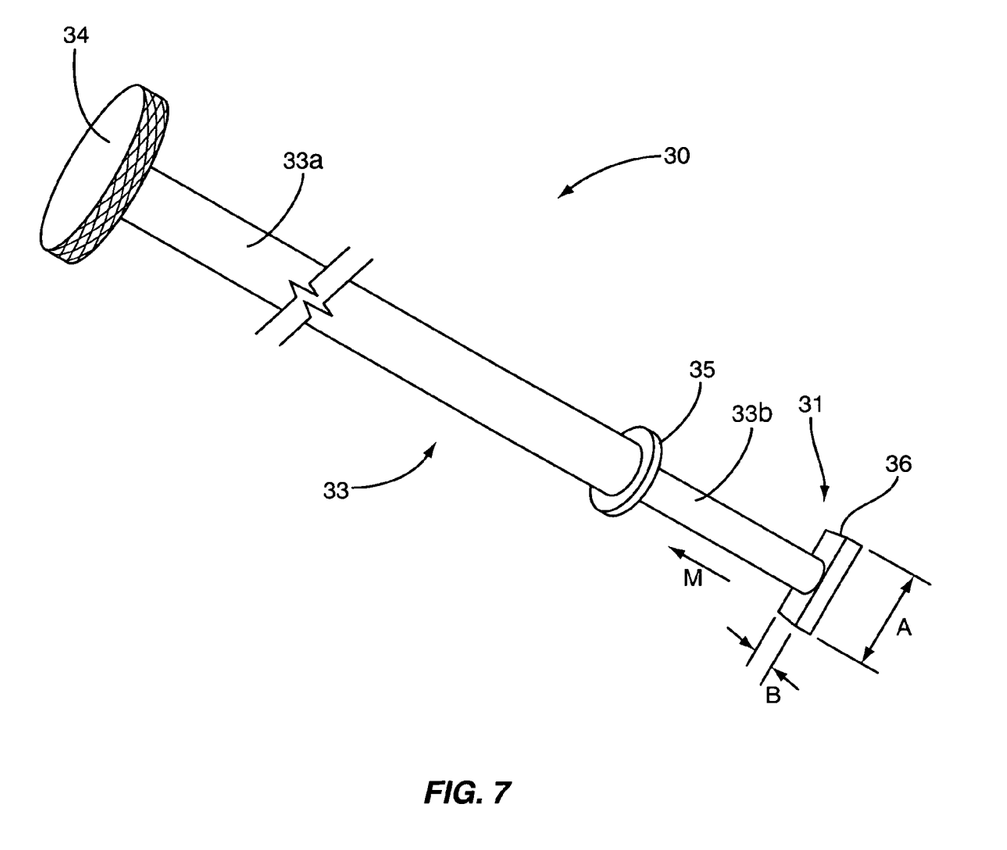
FIG. 7 is a perspective view of an insertion device according to one embodiment.

FIG. 7 illustrates another embodiment of an insertion device 30 having an elongated head 36. Head 36 has a shape with a dimension A greater than a dimension B. Body 33 comprises a first section 33a and a second section 33b. First section 33a is hollow and forms an outer sleeve that houses the second section 33b. A stop 35 is positioned towards a distal end of the first section 33a. Second section 33b has an elongated shape with an interior section that fits within the first section 33a. Head 36 is positioned at a distal end, and actuator 34 is positioned at the proximal end. The actuator 34 is operatively connected to the head 36 with actuation causing the head 36 to rotate.

Opening 22 within the implant 22 is sized to receive the head 36. As illustrated in FIG. 3, opening 22 has a first dimension X and a second dimension Y. These dimensions are sized to receive the head 36 with dimension X being greater than dimension B, and dimension Y being greater than dimension A. To connect the insertion device 30 with the implant 20, head 36 is positioned at an orientation to fit within the opening 22. Stop 35 is larger than the opening 22 and contacts the outer surface of the implant 20 to prevent over-insertion. Once the head 36 is inserted into the opening 22, head 36 is rotated about 90° with the dimension A now being substantially perpendicular to dimension X and preventing removal of the head 36 from the opening 22. Actuator 34 may further provide axial movement of the first section 33a relative to the second section 33b as illustrated by arrow M in FIG. 7. This axial movement causes the inner surface of the head 36 to contact the inner surface of the wall 21. Further, the stop 35 contacts the outer surface of the wall 21. Thus the implant 20 is compressed between the head 36 and stop 35 to remain connected to the insertion device 30.

The insertion device 30 may further be adjusted relative to the implant 20 by axially moving the head 36 away from the stop 35 to loosen the hold. Once loosened, insertion device 30 can be slid along the length of the opening 22 to another location and then re-tightened. The insertion device 30 remains connected to the implant 20 as long as the head 36 is rotated in a substantially perpendicular orientation relative to the opening 22.

The amount of relative rotation necessary to connect the head 36 within the opening 22 may vary and depend on the relative sizes of the head 36 and opening 22. In one embodiment, rotation of about 90° is necessary for the connection. In other embodiments, rotation of a lesser amount is adequate for connection.

Figure 8A:
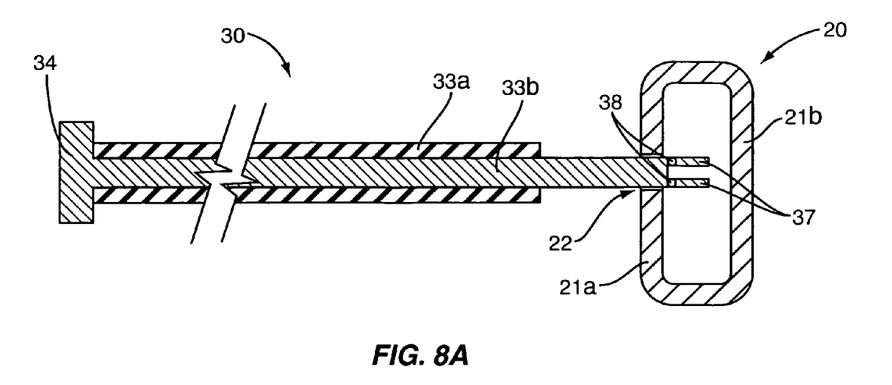
FIG. 8A is a cross-section view of an insertion device in a first orientation and positioned within an implant according to one embodiment.
Figure 8B:
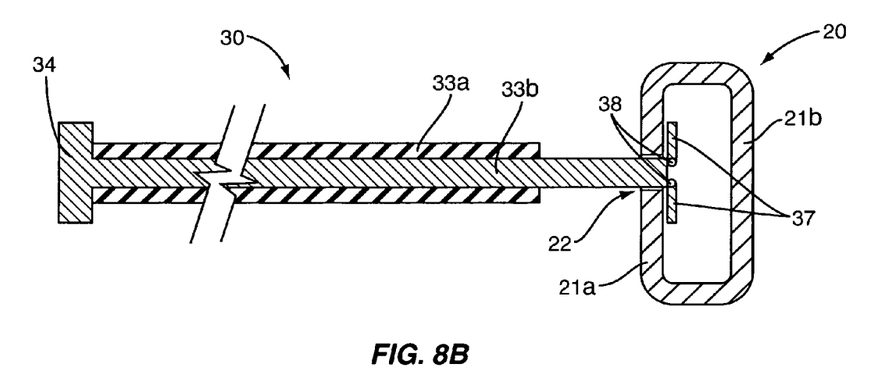
FIG. 8B is a cross-section view of an insertion device in a second orientation and positioned within an implant according to one embodiment.
Figure 8C:
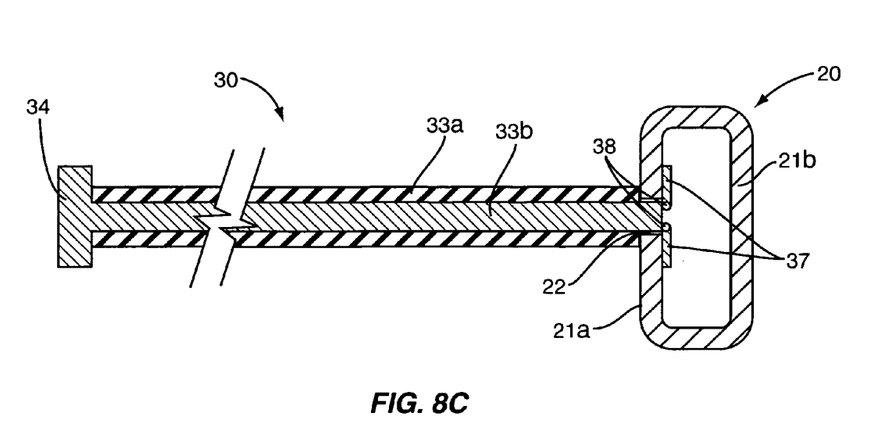
FIG. 8C is a cross-section view of an insertion device in a third orientation within an implant according to one embodiment.

Another embodiment of an insertion device 30 is illustrated in FIGS. 8A-8C. Insertion device 30 includes a first section 33a and a second section 33b. The distal end of the first section 33a includes a pair of extensions 37 that are movably attached at hinges 38. Extensions 37 are operatively connected to the actuator 34 that is manipulated to position the extensions at the desired orientation.

In the embodiment illustrated in FIGS. 8A-8C, a single hinge 38 is positioned along each extension 37. Additional hinges 38 may further provide for additional movement. Hinges 38 allow for the extensions 37 to move between a first orientation as illustrated in FIG. 8A to fit within the opening 22 in the implant 20. In this first orientation, the extensions 37 are aligned to be substantially parallel with a centerline of the insertion device 30. Insertion device 30 is inserted an amount such that the extensions 37 are within the outer wall 21a of the implant 20. Once inserted, actuator 34 is manipulated to move the extensions 37 outward and increase the overall width as illustrated in FIG. 8B. The extensions 37 are positioned at an angle relative to the centerline of the insertion device 30. The relative angles may vary depending upon the application. In the embodiment illustrated in FIGS. 8B and 8C, an angle of about 90° is formed between the extensions 37 and the insertion device 30.

The increased width of the extensions 37 in this orientation is now greater than the width of the opening 22 and prevents removal of the insertion device 30 from the implant 20. The inner surfaces of the extensions 37 may contact the inner surface of the outer wall 21a. Further manipulating of the actuator 34 causes relative movement between the inner and outer sleeves 33a, 33b. This movement compresses the outer wall 21a between the extensions 37 and outer sleeve 33a to lock the insertion device 30 to the implant 20 as illustrated in FIG. 8C.

The embodiment illustrated in FIGS. 8A-C includes a pair of extensions 37 mounted at the distal end of the insertion device 30. In another embodiment, a single extension 37 is mounted to the distal end to connect the insertion device 30 with the implant 20. When more than one extension 37 is used, extensions 37 may have the same or different sizes.

Opening 22 may be positioned at a variety of locations on the implant 20. In one embodiment as illustrated in FIG. 2, opening 22 is positioned along a narrowed end and extends along an elongated section. In another embodiment, opening 22 may extend along a majority of the implant 22. Further, the embodiment of FIG. 2 positions the opening 22 within an interior section of wall 21 with sections of the wall 21 extending on each side. In another embodiment, opening 22 is positioned on an upper or lower surface of the implant 20 such that it is not bordered on all sides. Opening 22 may extend completely through the wall 21 to access the interior section 23. In another embodiment as illustrated in FIGS. 8A-C, wall includes an outer section 21a and an inner section 21b. Opening 22 may extend through only the outer section 21a, or both sections.

Various embodiments include manipulation of an actuator 34 to engage the insertion device 30 with the implant 20. Other embodiments may include relative movement of the inner and outer sleeves 33a, 33b to cause the insertion device 30 to connect with the implant 20. By way of example, outer sleeve 33a may be grasped and slid distally along the inner sleeve 33b to engage the implant 20. Likewise, the outer sleeve 33a may be slid proximally along the inner sleeve 33b to disengage the implant 20. In another embodiment, body 33 is constructed of a single piece and movement of the distal end 31 requires movement of the entire body 33. By way of example, rotation of the distal end 31 is performed by rotating the entire body 33.

Implant 20 may be used in a variety of different applications. The embodiment of FIG. 1 illustrates the implant 20 being positioned within a disc space formed between adjacent vertebral members 100. The implant 20 may also have application to replace a section or entirety of a vertebral member. Implant 20 may also be inserted within various other parts of the body. The implant 20 may have a variety of different shapes and sizes. In one embodiment, implant 20 is substantially kidney shaped. In other embodiments, implant 20 has other shapes including circular, oval, polygonal, etc. In one embodiment, implant 90 is for use in intervertebral space between vertebral members.

Implant 20 may be inserted into the patient in a variety of different approaches. In one embodiment, implant 20 is inserted in a substantially lateral approach. In other embodiments, implant 20 is inserted with posterior and anterior approaches.

The term "distal" is generally defined as in the direction of the patient, or away from a user of a device. Conversely, "proximal" generally means away from the patient, or toward the user. Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting.

The present invention may be carried out in other specific ways than those herein set forth without departing from the scope and essential characteristics of the invention. In the embodiment illustrated in FIG. 5, multiple openings 27 are positioned opposite from opening 27. In another embodiment, a single opening 27 is positioned opposite from opening 22. The present embodiments are, therefore, to be considered in all respects as illustrative and not restrictive, and all changes coming within the meaning and equivalency range of the appended claims are intended to be embraced therein.

What is claimed is:

1. An intervertebral implant configured to engage with an insertion device for insertion between first and second vertebral members, the implant comprising:
   a body sized to fit between the vertebral members and including a sidewall with a superior surface configured to contact against the first vertebral member and an inferior surface configured to contact against the second vertebral member, a height of the body measured from the inferior surface to the superior surface;

an opening extending through the sidewall between the superior and inferior surfaces, the opening including an elongated shape with a first end and a second end, and a length measured from the first end to the second end that is greater than a height of the opening and the height of the body, the opening further including an entrance at an exterior side of the sidewall; and a connection member including a receptacle and being contained within the sidewall and prevented from being removed through the opening with the receptacle being sized to receive the insertion device;

a length of the connection member being less than the length of the opening for the connection member to be movable to positions along the length of the opening between a first orientation with the connection member in contact with the first end of the opening and spaced from the second end, and a second orientation with the connection member in contact with the second end of the opening and spaced from the first end;

the receptacle remaining between the first and second ends at each of the first and second orientations.

2. The implant of claim 1, wherein the connection member is mounted within the sidewall of the body.

3. The implant of claim 2, wherein a distal section of the connection member extends into an interior section of the body formed within the sidewall.

4. The implant of claim 1, wherein the body forms an interior section that is bounded within the sidewall, the connection member being positioned within the interior section and attached to an interior surface of the sidewall.

5. The implant of claim 1, wherein the connection member is constructed of a dissipating material.

6. The implant of claim 1, further comprising a second connection member attached to the body and configured to be movable along the length of the opening.

7. The implant of claim 1, wherein the receptacle extends a limited distance into a proximal end of the connection member and an opposing distal end, the connection member including a conical shape with the distal end being larger than the proximal end.

8. The implant of claim 1, wherein the connection member is configured to slide along a perimeter of the body.

9. The implant of claim 1, wherein the connection member is movable along the length of the opening without moving towards an interior of the body.

10. An intervertebral implant configured to engage with an insertion device for insertion between first and second vertebral members, the implant comprising:
    a body sized to fit between the vertebral members and including a sidewall with a first surface configured to contact against the first vertebral member and a second surface configured to contact against the second vertebral member, a height of the body measured between the first and second surfaces;
    an opening extending through the sidewall and including an exterior edge at an exterior of the sidewall, the opening positioned in the body between the first and second surfaces and including a first end and a second end, and a length measured from the first end to the second end; and
    a connection member including a housing with an inwardly-extending receptacle that is sized to receive the insertion device, the connection member attached to the body with the receptacle facing outward away from the body;
    the connection member being connected within the sidewall of the body and configured to be prevented from being removed from the body and movable along the length of the opening at the positions along the length;
    the connection member contained within the opening between the first and second ends with the receptacle remaining between the first and second ends; and
    the length of the opening being at least twice as long as a length of the connection member.

11. The implant of claim 10, wherein the opening includes a superior edge that is substantially parallel with the first surface and an inferior edge that is substantially parallel with the second surface.

12. The implant of claim 10, wherein the connection member is positioned at least partially between first and second surfaces of the opening.

13. The implant of claim 10, wherein the connection member is constructed of a dissipating material.

14. The implant of claim 10, wherein the connection member is positioned between the first and second surfaces of the opening and includes a greater thickness than the sidewall.

15. An intervertebral implant configured to engage with an insertion device for insertion between first and second vertebral members, the implant comprising:
    a body with an exterior wall that extends around and forms an interior section, the body including a first surface configured to contact the first vertebral member and a second surface configured to contact the second vertebral member;
    a slot extending through the exterior wall and including an elongated shape with a first end and a second end, and a height measured between the first and second surfaces;
    a connection member attached to the body and being movable along a length of the slot while remaining at the exterior wall and without moving towards the interior section of the body, the connection member including a receptacle sized to receive the insertion device; and
    the connection member including a height that is greater than the height of the slot to allow movement of the connection member along the length of the slot and to retain the connection member within the slot so that the receptacle remains within the slot and between the first and second ends after removal of the insertion device;
    wherein the connection member includes a conical shape with a first end that includes the receptacle being larger than an opposing second end.

16. The implant of claim 15, wherein the connection member is positioned within the interior section.

17. The implant of claim 15, wherein at least a portion of the connection member is positioned in the slot.

* * * * *